United States Patent
Levi et al.

(10) Patent No.: US 10,278,982 B2
(45) Date of Patent: May 7, 2019

(54) METHOD OF TREATING HETEROTOPIC OSSIFICATION

(71) Applicant: THE REGENTS OF THE UNIVERSITY OF MICHIGAN, Ann Arbor, MI (US)

(72) Inventors: Benjamin Levi, Ann Arbor, MI (US); Shailesh Agarwal, Ypsilanti, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/373,959

(22) Filed: Dec. 9, 2016

(65) Prior Publication Data

US 2017/0182079 A1  Jun. 29, 2017

Related U.S. Application Data (60) Provisional application No. 62/387,439, filed on Dec. 24, 2015.

(51) Int. Cl.
| | | |
|---|---|---|
| A61K 31/198 | (2006.01) | |
| A61K 31/436 | (2006.01) | |
| A61K 31/7048 | (2006.01) | |

(52) U.S. Cl.
CPC ........ *A61K 31/7048* (2013.01); *A61K 31/198* (2013.01); *A61K 31/436* (2013.01)

(58) Field of Classification Search
None
See application file for complete search history.

(56) References Cited

PUBLICATIONS

Zimmermann, Injury, Int. J. Care Injured 44 (2013) 570-575.*
Lin, Molecular Therapy, vol. 19, Issue 8, Aug. 2011, pp. 1426-1432.*
Werner, HSSF (2013) 9:166-170.*
Nursing Times, The administration of medicines, internet article, https://www.nursingtimes.net/clinical-archive/medicine-management/the-administration-of-medicines/288560.article, Nov. 19, 2007.*
Asai et al., Tendon progenitor cells in injured tendons have strong chondrogenic potential: the CD105-negative subpopulation induces chondrogenic degeneration. Stem cells, 32: 3266-77 (2014).
Barna et al., Gli3 and Plzf cooperate in proximal limb patterning at early stages of limb development. Nature, 436: 277-81 (2005).
Cobb et al., Application of genome-wide expression analysis to human health and disease. Proc. Natl. Acad. Sci. USA, 102: 4801-6 (2005).
Desai et al., Dissecting inflammatory complications in critically injured patients by within-patient gene expression changes: a longitudinal clinical genomics study. PLoS Med. 8:e1001093 (2011).
Koh et al., Molecular mechanisms for the activity of PX-478, an antitumor inhibitor of the hypoxia-inducible factor-1alpha. Mol. Cancer Ther, 7(1): 90-100 (2008).
Land et al., Hypoxia-inducible factor 1alpha is regulated by the mammalian target of rapamycin (mTOR) via an mTOR signaling motif. J. Biol. Chem. 282: 20534-43 (2007).
Laplante et al., mTOR signaling in growth control and disease. Cell, 149(2): 274-93 (2012).
Levi et al., Risk factors for the development of heterotopic ossification in seriously burned adults: A National Institute on Disability, Independent Living and Rehabilitation Research burn model system database analysis. J. Trauma Acute Care Surg. 79: 870-6 (2015).
Massoud et al., Design, Synthesis and Biological Evaluation of Novel HIF1α Inhibitors. Anticancer Res. 35(7): 3849-59 (2015).
Peterson et al., Burn injury enhances bone formation in heterotopic ossification model. Ann. Surg. 259: 993-8 (2014).
Peterson et al., Treatment of heterotopic ossification through remote ATP hydrolysis. Sci. Transl. Med. 6: 255ra132 (2014).
Prior et al., Sequence variation in hypoxia-inducible factor 1alpha (HIF1A): association with maximal oxygen consumption. Physiol. Genomics, 15(1): 20-6 (2003).
Provot et al., Hif-1alpha regulates differentiation of limb bud mesenchyme and joint development. J. Cell Biol. 177: 451-64 (2007).
Qian et al., Class II histone deacetylases are associated with VHL-independent regulation of hypoxia-inducible factor 1 alpha. Cancer Res. 66: 8814-21 (2006).
Rajicic et al., Identification and interpretation of longitudinal gene expression changes in trauma. PloS One, 5: e14380 (2010).
Sauer et al., Conserved sequence motifs and the structure of the mTOR kinase domain. Biochem. Soc. Trans. 41: 889-95 (2013).
Vanden Bossche et al., Heterotopic ossification: a review. J. Rehabil. Med. 27: 129-36 (2005).
Yu et al., BMP type I receptor inhibition reduces heterotopic [corrected] ossification. Nat. Med. 14: 1363-9 (2008).
Zhang et al., Digoxin and other cardiac glycosides inhibit HIF-1alpha synthesis and block tumor growth. Proc. Natl. Acad. Sci. USA, 105: 19579-86 (2008).
Zhao et al., Inhibition of HIF-1α by PX-478 enhances the antitumor effect of gemcitabine by inducing immunogenic cell death in pancreatic ductal adenocarcinoma. Oncotarget. 6: 2250-62 (2015).

* cited by examiner

*Primary Examiner* — Layla D Berry
(74) *Attorney, Agent, or Firm* — Marshall, Gerstein & Borun LLP (57) ABSTRACT

The invention provides a method of treating heterotopic ossification in a subject in need thereof. The method comprises administering a hypoxia inducible factor-1α (Hif-1α) inhibitor to the subject. In various embodiments, the Hif-1α inhibitor is PX-478, rapamycin, or digoxin.

5 Claims, 6 Drawing Sheets
Specification includes a Sequence Listing.

| Gene | Enterez ID | Fold Change |
|---|---|---|
| CDH5 | 12562 | 1.795 |
| FLT1 | 14254 | 1.693 |
| HIF1A | 15251 | 2.103 |
| PECAM1 | 18613 | 1.823 |
| TEK | 21687 | 1.83 |
| VWF | 22371 | 2.004 |

SEQUENCE LISTING

```
<160> NUMBER OF SEQ ID NOS: 6

<210> SEQ ID NO 1
<211> LENGTH: 22
<212> TYPE: DNA
<213> ORGANISM: Mus musculus
<220> FEATURE:
<221> NAME/KEY: misc_feature
<223> OTHER INFORMATION: Hif1 alpha- forward primer

<400> SEQUENCE: 1
gtcccagcta cgaagttaca gc                                              22

<210> SEQ ID NO 2
<211> LENGTH: 22
<212> TYPE: DNA
<213> ORGANISM: Mus musculus
<220> FEATURE:
<221> NAME/KEY: misc_feature
<223> OTHER INFORMATION: Hif1 alpha- reverse primer

<400> SEQUENCE: 2
cagtgcagga tacacaaggt tt                                              22

<210> SEQ ID NO 3
<211> LENGTH: 20
<212> TYPE: DNA
<213> ORGANISM: Mus musculus
<220> FEATURE:
<221> NAME/KEY: misc_feature
<223> OTHER INFORMATION: Sox9- forward primer

<400> SEQUENCE: 3
agtacccgca tctgcacaac                                                 20

<210> SEQ ID NO 4
<211> LENGTH: 20
<212> TYPE: DNA
<213> ORGANISM: Mus musculus
<220> FEATURE:
<221> NAME/KEY: misc_feature
<223> OTHER INFORMATION: Sox9- reverse primer

<400> SEQUENCE: 4
acgaagggtc tcttctcgct                                                 20

<210> SEQ ID NO 5
<211> LENGTH: 20
<212> TYPE: DNA
<213> ORGANISM: Mus musculus
<220> FEATURE:
<221> NAME/KEY: misc_feature
<223> OTHER INFORMATION: Acan- forward primer

<400> SEQUENCE: 5
actgcgacat ctggagtgac                                                 20
```

```
<210> SEQ ID NO 6
<211> LENGTH: 20
<212> TYPE: DNA
<213> ORGANISM: Mus musculus
<220> FEATURE:
<221> NAME/KEY: misc_feature
<223> OTHER INFORMATION: Acan- reverse primer

<400> SEQUENCE: 6
ctgtccactg ccaaagagaa                                             20
```

METHOD OF TREATING HETEROTOPIC OSSIFICATION

CROSS-REFERENCE TO RELATED APPLICATIONS

This application claims priority to U.S. Provisional Patent Application No. 62/387,439, filed Dec. 24, 2015, the disclosure of which is incorporated by reference.

STATEMENT OF GOVERNMENT INTEREST

This invention was made with government support under GM109105 awarded by the National Institutes of Health. The government has certain rights in the invention.

TECHNICAL FIELD OF THE INVENTION

The disclosure relates to methods for treating heterotopic ossification.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 50313A_Seqlisting.txt; Size: 1,488 bytes, created: Dec. 6, 2016.

BACKGROUND OF THE INVENTION

Heterotopic ossification (HO) is the pathologic formation of extra-skeletal bone in soft tissues. Vanden Bossche and Vanderstraeten, *J Rehabil Med* 27, 129 (2005). This process occurs in patient populations with severe trauma including large-surface area burns, musculoskeletal injury, orthopedic operations, and spinal cord injury, and in patient populations with a genetic disease known as fibrodysplasia ossificans progressiva (FOP). FOP is caused by a hyper-activating mutation in the type I bone morphogenetic protein (BMP) receptor ACVR1, and patients with FOP develop ectopic bone lesions in the absence of any substantial trauma. The clinical sequela of these pathologic ectopic bone formations, whether in the setting of trauma or genetic mutations, include non-healing wounds, chronic pain, and joint immobility. In the case of FOP, progressive ossification may lead to death due to loss of thoracic cage compliance.

Treatment options for HO are limited as bone often recurs following surgical resection, and some patients may have non-resectable HO due to its sensitive location. The risk of an operation may outweigh the benefits of excision, especially in the face of recurrence. There is a need for therapeutic options which can prevent HO before its initial occurrence in at-risk patients.

SUMMARY OF THE INVENTION

The invention includes, for example, a method of treating heterotopic ossification in a subject in need thereof, the method comprising administering a hypoxia inducible factor-1α (Hif-1α) inhibitor to the subject. In various embodiments, the Hif-1α inhibitor is PX-478, rapamycin, or digoxin.

The invention also includes a method of treating heterotopic ossification in a subject in need thereof, wherein the method comprises administering a mechanistic target of rapamycin (mTor) inhibitor to the subject.

In various embodiments, the heterotopic ossification is genetic, and the subject optionally suffers from fibrodysplasia ossificans progressiva. In an alternative embodiment, the heterotopic ossification results from trauma, such as burns, musculoskeletal injury, orthopedic operations (e.g., post total hip replacements, post joint arthroplasty), spinal cord injury, stroke, poliomyelitis, myelodysplasia, carbon monoxide poisoning, spinal cord tumors, syringomyelia, tetanus, or multiple sclerosis.

DETAILED DESCRIPTION OF THE INVENTION

The invention is predicated, at least in part, on the discovery that Hif1α inhibitors, such as rapamycin or PX-478, potently diminish extra-skeletal bone formation in different models of HO. A method of treating heterotopic ossification in a subject in need thereof is provided by the disclosure. The method comprises administering a hypoxia inducible factor-1α (Hif-1α) inhibitor to the subject. HIF-1α is a component of the HIF transcription factor heterodimer and has been well characterized. See, e.g., Prior et al., *Physiological Genomics* 15(1), 20 (2003). Examples of Hif-1α inhibitors include, but are not limited to, PX-478 (S-2-amino-3-[4'-N,N,-bis(chloroethyl)amino]phenyl propionic acid N-oxide dihydrochloride, described in, e.g., Koh et al., *Mol Cancer Ther* 7(1), 90 (2008)), rapamycin, and digoxin. Other Hif-1α inhibitors include, e.g., CJ-3k and derivatives thereof (described in, e.g., Massoud et al., *Anticancer Res.* 35(7), 3849-59 (2015)), echinomycin, topotecan, LAQ824 (described in, e.g., Qian et al., *Cancer Res* 66, 8814 (2006)), metformin, imatinib, ouabain, and proscillaridin, and additional inhibitors are known in the art. In various embodiments, the Hif-1α inhibitor is not siRNA or an antisense oligonucleotide. The Hif-1α inhibitor need not completely inhibit Hif-1α to achieve a therapeutic effect; the inhibitor preferably inhibits Hif-1α activity by at least 50% (e.g., 50%-99%), at least 60%, at least 70%, at least 80%, at least 90%, or at least 95%. The inhibitor may inhibit or reduce Hif-1α protein levels, activation, deubiquitination, and the like to inhibit Hif-1α activity.

Additionally, the invention includes a method of treating heterotopic ossification in a subject in need thereof, wherein the method comprises administering a mechanistic target of rapamycin (mTor) inhibitor to the subject. mTor is a serine/threonine protein kinase of the phosphatidylinositol 3-kinase-related kinase protein family, and is well characterized. See, e.g., Laplante et al., *Cell* 49(2), 274 (2012); Sauer et al., *Biochem Soc Trans* 41, 889 (2013). Examples of mTor inhibitors include, but are not limited to, rapamycin, temsirolimus, everolimus, deforolimus, vincristine, zotarolimus, 32 deoxy-rapamycin, NVP-BEZ235, BGT226, SF1126, PKI-587, INK128, AZD8055, AZD2014, GNE477 (a thienopyrimidine), PI-103 (a tricyclic pyridofuropyrimidine), XL765, WJD008 (a 5-cyano-6-morpholino-4-substituted pyrimidine analogue), PP242, PP30, Torin1, WYE-354, WAY-600, WYE-687, Ku-0063794, curcumin, resveratrol, epigallocatechin gallate, genistein, 3,3-diindolylmethane, and caffeine.

In various embodiments, the heterotopic ossification is genetic, and the subject optionally suffers from fibrodysplasia ossificans progressiva. In an alternative embodiment, the heterotopic ossification results from trauma, such as burns, musculoskeletal injury, orthopedic operations, or spinal cord injury. Thus, in various aspects, the subject is suffering from heterotopic ossification or is at risk of suffering from heterotopic ossification (e.g., is genetically predisposed to formation of ectopic bone lesions, has been subjected to trauma, etc.). In various embodiments, the method comprises administering to the subject the Hif-1α inhibitor (and/or an mTor inhibitor) in an amount and under conditions effective to treat, in whole or in part, heterotopic ossification. "Treating" heterotopic ossification includes (but is not limited to) the prevention or slowing of the formation or progression of heterotopic ossification in a subject and/or reduction or delaying the onset of symptoms associated with heterotopic ossification. It will be appreciated that the method need not completely prevent or halt the progression of heterotopic ossification to achieve a beneficial (e.g., therapeutic) effect. Any inhibition of the onset or progression of heterotopic ossification or severity of symptoms associated with heterotopic ossification is contemplated. For example, any reduction in the formation of lamellar bone inside soft-tissue structures where bone does not normally exist is contemplated.

Methods of determining the efficacy of the method in treating heterotopic ossification are known in the art and described herein. For example, the progression of heterotopic ossification is monitored using x-ray, bone scan, subject range of motion, prostaglandin E2 excretion in 24-hour urine, ultrasonography, and/or evaluating joint swelling or pain.

The invention further includes use of a Hif-1α inhibitor and/or mTor inhibitor in the treatment of heterotopic ossification. For example, a Hif-1α inhibitor and/or mTor inhibitor can be used in the manufacture of a medicament for the treatment of heterotopic ossification, as described in detail herein.

The Hif-1α inhibitor can be administered in combination with other active agents or therapeutic modalities, including, but not limited to, anti-inflammatory agents, pain relievers, radiation therapy, and physical therapy. Similarly, an mTor inhibitor can be administered in combination with other active agents or therapeutic modalities, including, but not limited to, anti-inflammatory agents, pain relievers, radiation therapy, and physical therapy.

Example

This Example demonstrates the ability of HIF-1α inhibitors to treat both trauma-induced and genetic-based heterotopic ossification in clinically relevant animal models and provides further description of the method of the invention.

Materials and Methods

Patient Enrollment and Sampling for Gene Expression Profiling:

Patient enrollment and sample collection for patients have been described previously. Cobb, J. P., et al. *Proceedings of the National Academy of Sciences of the United States of America* 102, 4801-4806 (2005). 244 burn patients were enrolled between 2000 and 2009 at one of four burn centers. If admission occurred within 96 hours post-injury, at least 20% of the TBSA was affected, and at least one excision and grafting procedure was required. Additionally, 35 healthy control subjects (16-55 y) were recruited between 2004 and 2007. In both the burn patients and the control patients, adipose tissue was collected and analyzed for RNA transcript levels. Using a fine scissor or scalpel, 80 mg of adipose tissue was obtained and immediately placed on an iced petri dish and cut into a 2-5 mm cube. The sample was placed in a cryogenic tube containing 2 ml RNAlater to stabilize the tissue according to Standard Operating Procedure (SOP) B001.03, the tissue was processed to total cellular RNA using a commercial RNA purification kit (RNeasy, Qiagen, Valencia, Calif.) according to SOP G026.01. Biotinylated cRNA was generated from 4 µg of total cellular RNA, hybridized onto HU133 Plus 2.0 GeneChips (Santa Clara, Calif.), stained and washed according to the manufacturer's recommendations. A total of 25,000 genes were queried of which 3,500 were significantly changed with a false discovery rate (FDR) <0.001 and defined fold change ≥1.5.

Analysis of Time-Course Gene Expression Data:

Specimens were immediately stabilized using RNAlater (Ambion). Total cellular RNA was extracted from the remaining specimens with good quality using a commercial RNA purification kit (RNeasy, Qiagen). Biotinylated cRNA was generated from 1 µg of total cellular RNA using the 3' IVT Express Kit and protocol of Affymetrix, and hybridized onto an HU133 Plus 2.0 GeneChip (Affymetrix). EDGE (Extraction of Differential Gene Expression) was used to estimate the significance of expression changes for each gene by 1,000 random permutations. Significant genes were selected by FDR <0.001 and fold change ≥1.5. These genes were further analyzed using Ingenuity Pathway Analysis36.

Animals:

Mice included for extra-skeletal bone evaluation were wild type C57BL/6 (Charles River Laboratory), Cdh5-Cre/tdTomatofl/wt, Prx-Cre/Hif1αfl/fl, Prx-Cre/ROSA26mTmG, caAcvr1fl/fl, Nfatc1-Cre/caAcvr1fl/wt, or littermate controls. Tail genomic DNA was used for genotyping. Mice used for bioluminescent imaging were homozygous for the ODD-luc transgene. In these mice, the C-terminal portion of the hypoxia-inducible factor 1 alpha oxygen-dependent degradation domain (ODD) is fused to the firefly luciferase (luc) gene. Hypoxia causes stabilization of the fusion protein thereby increasing fluorescence upon luciferin administration.

Extra-Skeletal Bone Models:

All mice received pre-surgical analgesia consisting of 0.1 mg/kg buprenorphine, followed by anesthesia with inhaled isoflurane, and close post-operative monitoring with analgesic administration. Burn/tenotomy mice received a 30% total body surface area (TBSA) partial-thickness burn on the shaved dorsum followed by left hindlimb Achilles' tendon transection. The dorsum was burned using a metal block heated to 60° C. in a water bath and applied to the dorsum for 18 seconds continuously. The tenotomy site was closed with a single 5-0 vicryl stitch placed through the skin only. caAcvr1fl:fl mice received hindlimb cardiotoxin and Ad.cre injection at P24. Mice were then euthanized after 22 days (PX-478) or 15 days (rapamycin). Separate controls were used for each drug treatment to account for differences in the day of euthanization. Nfatc1-Cre/caAcvr1fl:wt mice were generated by crossing Nfatc1-Cre+ mice with caAcvr1fl:wt mice. Resulting mutants developed extra-skeletal bone by P4-5.

Drug Treatment:

Burn/tenotomy or hybrid HO mice were administered PX-478 (100 mg/kg) or rapamycin (5 mg/kg) in PBS solution via intraperitoneal injection. Mice received injections every other day for the duration of the study. Nfatc1-Cre/caACVR1fl:wt mice were administered PX-478 (100 mg/kg) every other day for a total of 2 weeks.

Isolation and Culture of Mesenchymal Stem Cells:

Mouse mesenchymal stem cells (MSCs) were harvested from the tendon transection site originating from the calcaneus to the confluence of the fibula and tibia wild-type mice. All tissue was mechanically minced, and digested with collagenase A and dispase and subsequently plated. To test drug treatment on Hif1α expression, cells were cultured in a hypoxia chamber with 0.5% oxygen. Cell treatment with PX-478 (10 µM) or rapamycin (5 µM) was initiated 24 hours before hypoxia treatment and re-dosed in hypoxia for 24 hours. Protein was harvested and analyzed using Western blot for Hif1α and α-tubulin. To test effect of PX-478 treatment on chondrogenesis, cells isolated from the tendon were cultured in chondrogenic differentiation medium (PT-3925 & PT-4121, Lonza, Basel, Switzerland). All in vitro experiments were performed in biologic and technical triplicate.

Histology and Immunofluorescence:

Histologic evaluation was performed at indicated time points in burn/tenotomy, Ad.cre/cardiotoxin, or Nfatc1-Cre/ca-Acvr1fl:wt mutants. Hind limbs were fixed in formalin overnight at 4° C. and subsequently decalcified in 19% EDTA solution for 3-5 weeks at 4° C. until x-ray verification of decalcification. Hind limbs were paraffin- or cryo-embedded, and 5-7 µm sections were cut and mounted on Superfrost plus slides (Fisher) and stored at room temperature. Haematoxylin/eosin and Movat's pentachrome staining were performed of the ankle region. Immunostaining staining of extra-skeletal ectopic bone was performed on rehydrated wax sections with the following primary antibodies: mouse anti-mouse anti-Hif1α (Santa Cruz, Cat No. 53546), goat anti-mouse anti-Cdh5 (Santa Cruz, Cat No. 6458), goat anti-mouse anti-pSmad 1/5 (Santa Cruz, Cat No. 12353), goat anti-mouse anti-CD31 (Santa Cruz, Cat No. 1506), rabbit anti-mouse anti-Sox9 (Santa Cruz, Cat No. 20095), or anti-mouse PDGFRα. Appropriate dilutions were determined prior to achieving final images. The appropriate fluorescent secondary antibody was applied and visualized using fluorescent microscopy. Secondary antibodies consisted of anti-rabbit or anti-goat Alexafluor-488(green) or -594(red). All mouse sections were taken 3 weeks after burn/tenotomy. All counts were performed by blinded observer with 15 high-power fields for each sample.

Fluorescent and Bioluminescent Imaging:

All fluorescent and bioluminescent imaging was acquired using a PerkinElmer IVIS Spectrum system. Wild type C57BL/6 mice were used for fluorescent imaging to assess vascular perfusion. Mice were administered Angiosense 750 EX via tail vein injection. Fluorescent imaging was acquired 24 hours after injection at 770 nm wavelength. ODD-luc were used for all bioluminescent imaging. Mice received luciferin i.p. injection ten minutes prior to imaging.

Quantitative PCR:

Tissue was harvested from the tenotomy site of burn/tenotomy mice, or from the corresponding contralateral, control hindlimb at indicated time points. RNA was collected from tissue using RNeasy Mini Kit (Qiagen, Germantown, Md.) according to manufacturer's specifications. Reverse transcription was performed with 1 µg RNA using Taqman Reverse Transcription Reagents (Applied Biosystems, Foster City, Calif.). Quantitative real-time PCR was carried out using the Applied Biosystems Prism 7900HT Sequence Detection System and Sybr Green PCR Master Mix (Applied Biosystems). Specific primers for these genes were chosen based on their PrimerBank sequence (Table 1).

TABLE 1

Quantitative PCR primers.

| Species | Name | Accession Number | Primer Sequence (5'→3')* | SEQ ID NO |
|---|---|---|---|---|
| Mouse | Hif1α | NM_176958 | F-GTCCCAGCTACGAAGTTACAGC<br>R-CAGTGCAGGATACACAAGGTTT | 1<br>2 |
| | Sox9 | NM_011448 | F-AGTACCCGCATCTGCACAAC<br>R-ACGAAGGGTCTCTTCTCGCT | 3<br>4 |
| | Acan | NM_007424 | F-ACTGCGACATCTGGAGTGAC<br>R-CTGTCCACTGCCAAAGAGAA | 5<br>6 |

*"F" denotes a forward primer. "R" denotes a reverse primer.

μCT and Nano-CT Analysis:

μCT scans (Siemens Inveon using 80 kVp, 80 mA, and 1,100 ms exposure) were used to quantify extra-skeletal bone growth in burn/tenotomy, Ad.cre/cardiotoxin, or mutant Nfatc1-cre/caAcvr1fl:wt mice. Burn/tenotomy mice received scans at 5 and 9 weeks after tenotomy. Ad.cre/cardiotoxin mice received μCT scans at day 22 after induction with Ad.cre and cardiotoxin injection. Nfatc1-cre/caAcvr1fl:wt mice and littermate controls received μCT scansat day 13 after birth. Images were reconstructed and HO volume quantified using a calibrated imaging protocol as previously described with the MicroView μCT viewer (Parallax Innovations, Ilderton, Canada).

Microscopy:

All fluorescently stained images were taken using an Olympus BX-51 upright light microscope equipped with standard DAPI, 488 nm, and TRITC cubes attached to an Olympus DP-70 high resolution digital camera. Each site was imaged in all channels and overlaid in DPViewer before examination in Adobe Photoshop.

Statistical Analysis:

A power analysis was first performed to determine how many mice were needed for our PX-478 treatment groups. For power analysis, the primary outcome of interest is differences in HO volume with treatment. To confirm a 50% decrease in HO volume with power of 0.8, assuming a s.d. of 1.5 mm$^3$ and mean HO volume of 7.5 mm$^3$ in untreated mice, three mice per group were required. Means and SDs were calculated from numerical data, as presented in the text, figures, and figure legends. In figures, bar graphs represent means, whereas error bars represent one SD. Statistical analysis was performed using an appropriate analysis of variance when more than two groups were compared, followed by a post hoc Student's t test (with a Bonferroni correction) to directly compare two groups. Inequality of SDs was excluded by using the Levene's test. Outliers were excluded using the Grubb's test for outliers. p values are included in the figure legends.

Results

Figure 1A:
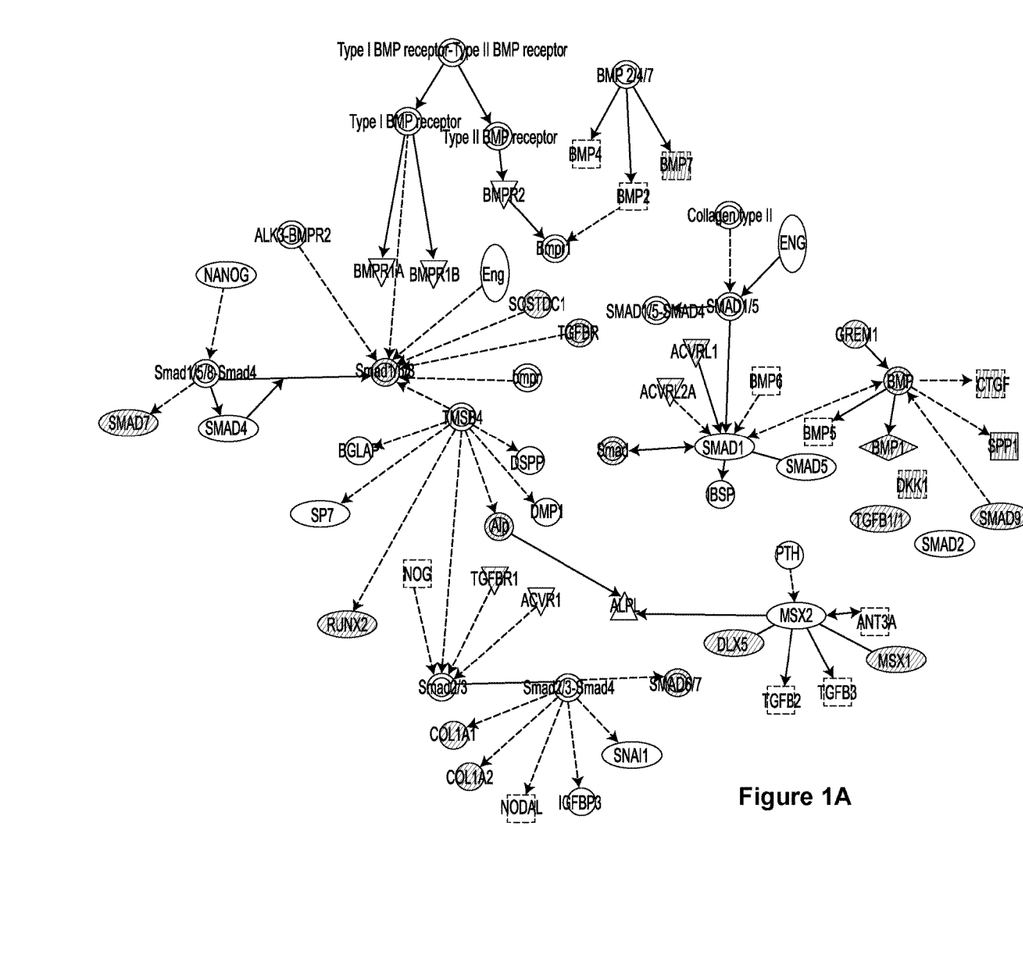
FIG. 1A illustrates ingenuity pathway analysis of mRNA transcripts isolated from adipose tissue from burn or unburned "control" patients.
Figure 1B:
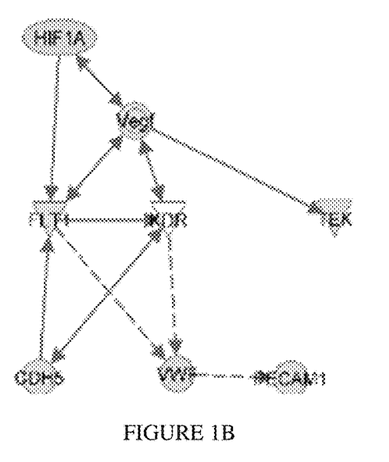
FIG. 1B is a diagram illustrating up-regulation of the pro-vasculogenic pathway including HIF1α, vWF, PECAM, FLT1, CDH5, and VEGF.
Figure 1C:
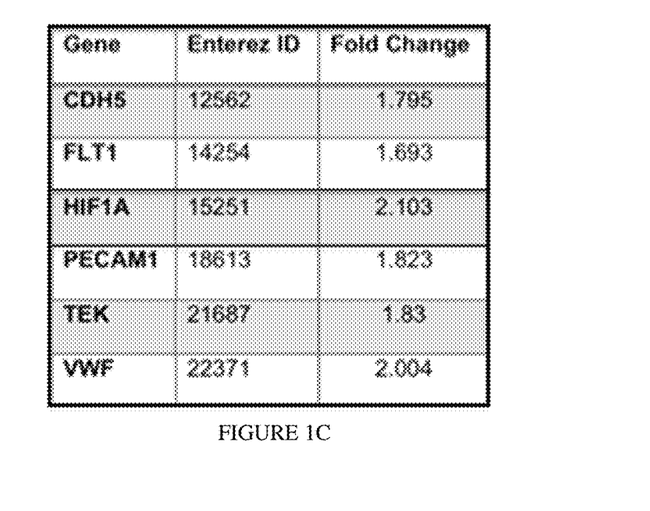
FIG. 1C is a chart showing the numeric-fold increase in gene expression of burn patients when compared with unburned, "control" patients.

Human Trauma Patients Exhibit Up-Regulation of HIF1α and Related Downstream Vascular Signaling Mediators:

A genomic database of 244 patients at high risk for HO due to large surface-area burns to compare with unburned "control" patients was examined. A total of 25,000 genes were queried, of which 3,500 were noted to be significantly different in tissue from burn patients when compared to control patients. A total of 25,000 genes were queried, of which 3,500 were noted to be significantly different in tissue from burn patients when compared to control patients. In particular, a significant up-regulation of HIF1α was observed, placing it within the top fifty up-regulated gene transcripts. In addition, related downstream gene transcripts including vWF, PECAM, FLT1, CDH5, and VEGF were up-regulated (FIG. 1A-C). In the evaluation of HIF1α, the Ingenuity Pathway Knowledgebase was queried for HIF1α downstream genes for which expression levels are previously known to be changed by activation of HIF1α. Rajicic, N., et al. PloS one 5, e14380 (2010); Desai, K. H., et al. PLoS medicine 8, e1001093 (2011). The expression level of HIF1α was significantly up-regulated after burns (fold change=2.103, FDR<0.05) with pathway activation z-score of 4.965 placing it within the top 50 up-regulated genes.

Figure 2A:
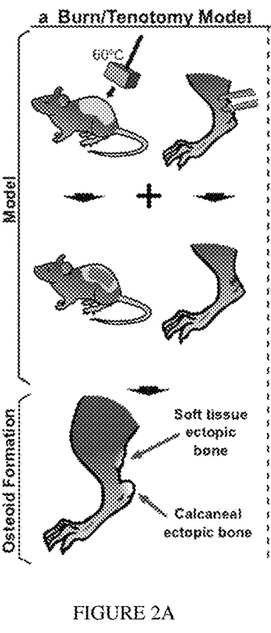
FIG. 2A illustrates a trauma-induced model of HO in which mice receive a 30% total body surface-area partial-thickness dorsal burn injury with hindlimb Achilles' tendon transection, resulting in HO formation along the calcaneus as well as proximally within the soft tissue.
Figure 2B:
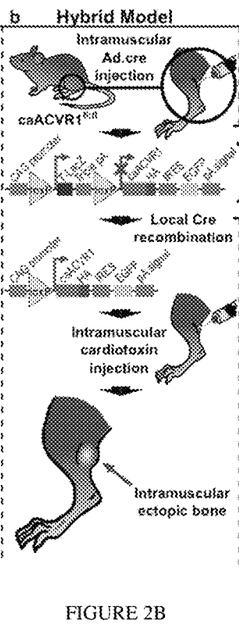
FIG. 2B illustrates a hybrid model of HO wherein Ad.cre and cardiotoxin are injected into the gastrocnemius muscle of caACVR1fl:fl mice resulting in intramuscular HO formation.
Figure 2C:
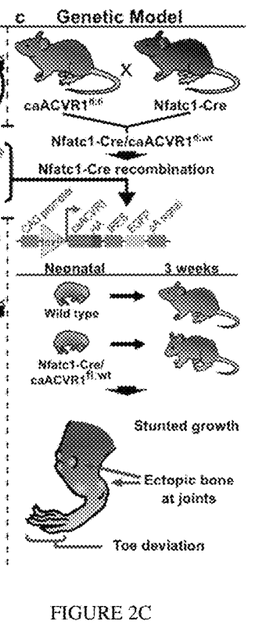
FIG. 2C illustrates the Nfatc1-Cre/caACVR1fl:wt mouse model, wherein mice develop HO generally localized to the joints 4-5 days after birth in a model of genetic HO.

HO in Three Separate Animal Models is Characterized by Elevated Hif1α Expression:

Three separate models of HO were studied—1) burn/tenotomy, 2) Ad.cre/cardiotoxin-inducible caACVR1 expression, and 3) congenital HO (Nfatc1-cre/caACVR1fl/wt) (FIG. 2A-C). Yu, P. B., et al. Nature medicine 14, 1363-1369 (2008); Peterson, J. R., et al. Science translational medicine 6, 255ra132 (2014); Peterson, J. R., et al. Annals of surgery 259, 993-998 (2014); Asai, S., et al. Stem cells 32, 3266-3277 (2014). Notably, when burn/tenotomy was performed in ODD-Luc Hif1α reporter mice, a highly positive signal at the tenotomy site was observed compared to the uninjured side, which indicates that the tenotomy site becomes highly hypoxic. Immunostaining for Hif1α confirmed its expression in each of these three models. Importantly, Hif1α was present during the pre-cartilage and immature HO phases in the burn/tenotomy model and slowly receded with the formation of mature HO. In the burn/tenotomy model, Hif1α co-localized with the chondrogenic marker Sox9, suggesting its intimate role in cartilage formation in this model. Within mature HO observed 9 weeks after trauma, Hif1α expression was present only within the marrow space of the heterotopic bone, but was no longer present within the osteoid or along the periphery of the HO lesion.

Similarly, HO lesions that developed in the Ad.cre/cardiotoxin model demonstrated a similar pattern of Hif1α expression with co-localization with Sox9 and pSmad 1/5, a known regulator of bone development.

To understand whether Hif1α plays a role in the formation of HO in the absence of inflammatory trauma, as in patients with hyperactive ACVR1, a model in which HO develops spontaneously due to constitutive activity of ACVR1 (Nfatc1-Cre/caACVR1fl:wt) was employed. Agarwal, S., et al. "BMP signaling mediated by constitutively active Activin type 1 receptor (ACVR1) results in ectopic bone formation localized to distal extremity joints." Developmental biology (2015). These mice spontaneously develop HO lesions within 4-5 days after birth without concomitant trauma or Ad.Cre or cardiotoxin injections. Lesions are generally localized to the joints including ankles, knees, elbows, and digits. Immunostaining confirmed robust Hif1α expression within immature HO also in this model, which indicates that Hif1α plays a role in HO formation in the setting of hyperactive BMP receptor signaling despite absence of inflammatory trauma. Again robust co-localization of Hif1α with Sox9 and pSmad 1/5 was noted.

Taken together, the data demonstrate that Hif1α expression is a common denominator in trauma-induced and genetic models of HO, and precedes cartilage formation and cartilage ossification, thereby validating it as a therapeutic target.

Pharmacologic Inhibition of Hif1α Limits HO after Burn/Tenotomy:

The ability of Hif1α inhibition to prevent HO was characterized using a representative Hif1α inhibitor, the drug PX-478, which has been shown to inhibit Hif1α transcription and translation. Zhao, T., et al. *Oncotarget* 6, 2250-2262 (2015). In vitro treatment of cells derived from the tenotomy site 3 weeks after injury (3WLST) and cultured in hypoxic conditions showed diminished levels of the Hif1α transcript and of the chondrogenic gene transcripts Sox9 and Acan upon treatment with PX-478. Additionally, PX-478 and rapamycin, also a Hif1α inhibitor, significantly diminished Hif1α produced by mesenchymal cells isolated from tendon, confirming again that these drugs affect Hif1α levels in cells local to the future HO site.

Figure 3A:
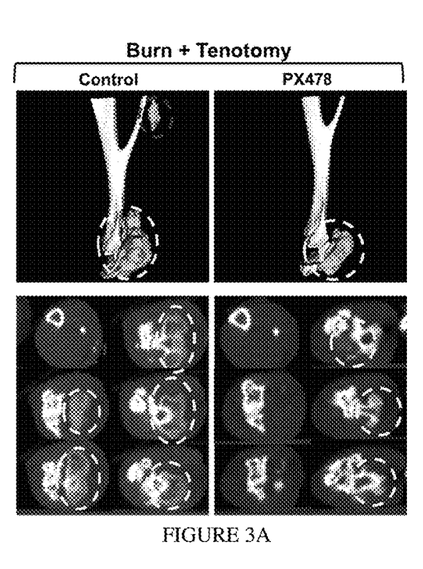
FIG. 3A depicts three-dimensional reconstruction and serial cross-sections of microCT scans of PX-478 and control-treated burn/tenotomy mice.
Figure 3B:
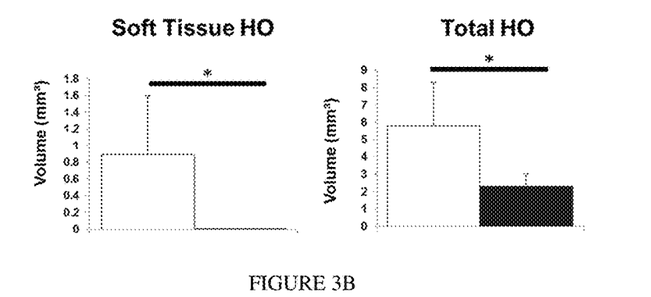
FIG. 3B are bar graphs illustrating soft tissue HO volume (y-axis ($mm^3$)) in a burn/tenotomy model (9 week volume: 0.90 $mm^3$ v. 0.00 $mm^3$, p=0.05; 9 week normalized volume: 1.0 v. 0.0, p=0.05; yes/no: $\chi2$=9.5, p<0.01) and total HO volume (y-axis ($mm^3$)) in burn/tenotomy mice (5 week volume: 4.3 $mm^3$ v. 1.5 $mm^3$, p<0.05; 9 week volume: 5.8 $mm^3$ v. 2.3 $mm^3$, p<0.05; 9 week normalized volume: 1.0 v. 0.4, p<0.05), in control-treated (left-hand bar) and PX-478-treated (right-hand bar) mice. PX-478 significantly decreased total HO volume and eliminated soft tissue HO.
Figure 3C:
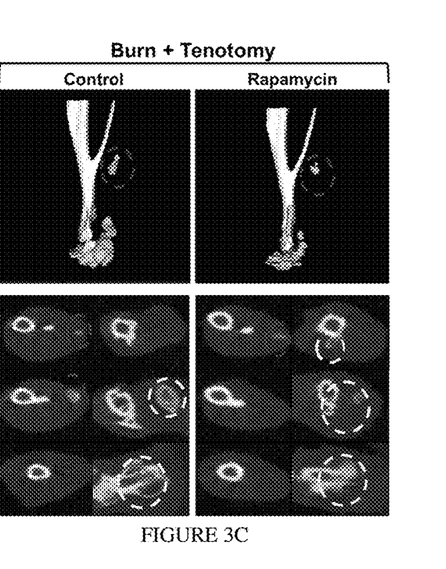
FIG. 3C depicts three-dimensional reconstruction and serial cross-sections of microCT scans of rapamycin and control-treated burn/tenotomy mice.
Figure 3D:
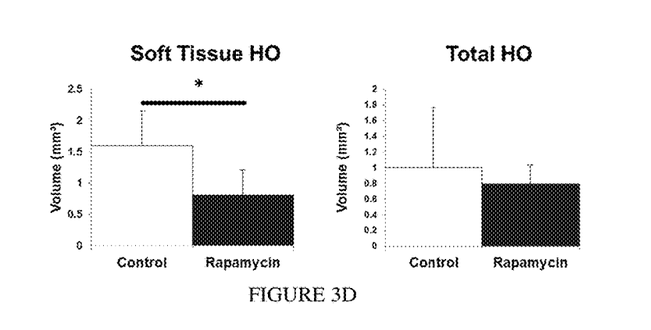
FIG. 3D are bar graphs illustrating soft tissue HO volume and total HO volume (y-axis ($mm^3$)) in a burn/tenotomy model of control-treated (left-hand bar) and rapamycin-treated (right-hand bar) mice. Rapamycin treatment significantly reduced de novo HO formation (9 week volume: 1.60 $mm^3$ v. 0.81 $mm^3$, p<0.05; 9 week normalized volume: 1.0 v. 0.51, p<0.05). *p<0.05 for volumetric measurements; † p<0.05 for binary analysis (yes/no). Arrow="soft tissue" heterotopic bone; light hashed circle=calcaneal heterotopic bone; n=3 for PX-478-treated mice; n=11 for PX-478 control mice; n=5 for rapamycin-treated mice; n=4 for rapamycin control mice.

Next, it was determined that treatment with PX-478 decreased Hif1α expression and cartilage formation in vivo, and consequently inhibited overall development of HO. Mice received burn/tenotomy and were subsequently treated with PX-478; histologic evaluation after 3 weeks confirmed a substantial decrease in the cartilage anlagen, which is typically present after 3 weeks. Furthermore, Hif1α expression diminished 3 weeks after injury. Consistent with these data, expression of Sox9 was considerably diminished in the PX-478 treated group. Moreover, burn/tenotomy mice treated with PX-478 demonstrated a significant reduction in total HO volume at 5 weeks (4.3 $mm^3$ v. 1.5 $mm^3$, $p<0.05$) and 9 weeks (5.8 $mm^3$ v. 2.3 $mm^3$, $p<0.05$) after injury. FIGS. 3A and 3B. Lastly, PX-478 treatment completely inhibited "soft tissue" HO—extra-skeletal bone, which forms within the proximal transected tendon and distal gastrocnemius but away from the calcaneus—after 9 weeks, as shown by binary analysis (yes/no; $\chi2=9.5$, $p<0.01$) and quantitative comparison (0.90 $mm^3$ v. 0.00 $mm^3$, $p=0.05$). FIG. 3B. This is notable, as "soft tissue" HO likely forms de novo without the influence of adjacent cartilage, bone, or periosteum normally located in close proximity to extra-skeletal bone at the calcaneus. Taken altogether, these findings suggest that Hif1α is a permissive factor for chondrogenesis and its inhibition can prevent transition of non-osteochondro progenitor lineage cells into cells forming cartilage and ultimately extra-skeletal bone. Notably, no adverse effects of PX-478 were observed on wound healing of the burn or at the hindlimb tenotomy sites. To test a second Hif1α inhibitor, mice were treated with rapamycin, resulting in significantly diminished de novo HO formation (1.60 $mm^3$ v. 0.81 $mm^3$, $p<0.05$). FIGS. 3C and 3D. Zhang, H., et al. *Proceedings of the National Academy of Sciences of the United States of America* 105, 19579-19586 (2008).

Figure 4A:
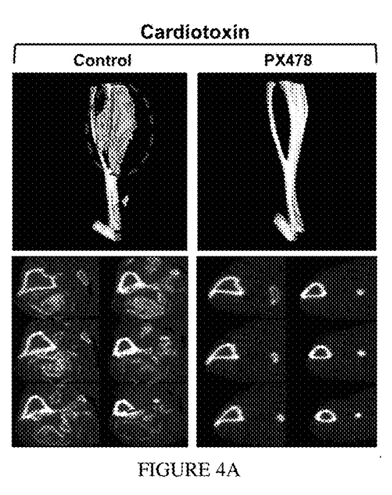
FIG. 4A depicts three-dimensional reconstructions and cross-sections of microCT scans of PX-478 and control-treated hybrid model mice.
Figure 4B:
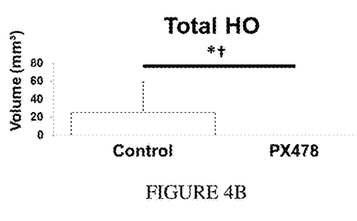
FIG. 4B is a bar graph illustrating total HO volume (y-axis) in control and PX-478-treated mice. PX-478 treated hybrid model mice produced almost no evidence of HO on microCT when compared with control-treated mice (Control: n=12 legs, PX-478: n=12 legs) (Volume: 18.1 mm³ v. 0.01 mm³, p=0.01; Normalized volume: 1.0 v. 0.0, p=0.01; yes/no: χ2=13.6, p<0.001).
Figure 4C:
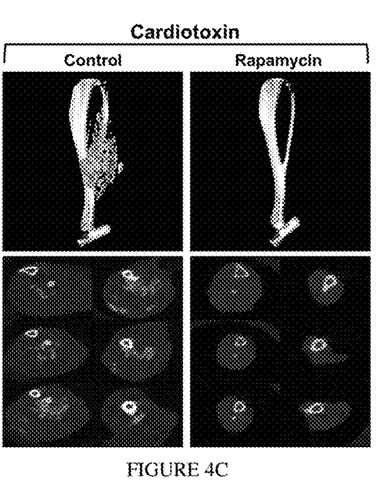
FIG. 4C depicts three-dimensional reconstructions and cross-sections of microCT scans of rapamycin and control-treated hybrid model mice.
Figure 4D:
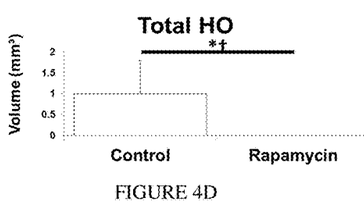
FIG. 4D is a bar graph illustrating total HO volume (y-axis) in control and rapamycin-treated mice. Rapamycin treated hybrid model mice produced no evidence of HO on microCT when compared with control-treated mice (Control: n=8 legs, Rapamycin: n=10 legs) (Volume: 17.5 mm³ v. 0.00 mm³, p<0.001; Normalized volume: 1.0 v. 0.0, p<0.05; yes/no: χ2=14.3, p<0.001).

Pharmacologic Inhibition of Hif1α Limits HO Caused by ACVR1 Constitutive Activity:

The findings described above were confirmed in models of constitutive ACVR1 activity caused by expression of the caACVR1 (ACVR1 Q207D) mutation. caACVR1fl/fl mice injected with cardiotoxin and Ad.cre develop robust HO and this model has been used to study inhibitors of ACVR1 signaling. caACVR1fl/fl mice treated with PX-478 demonstrated near elimination of cartilage or bone based on pentachrome staining after Ad.cre/cardiotoxin induction. Similarly, there was elimination of Hif1α and Sox9 based on immunostaining. Finally, microCT analysis confirmed the complete absence of HO in the PX-478 treated group based on binary analysis (yes/no; $\chi2=13.6$, $p<0.001$) and quantitative comparison (18.1 $mm^3$ v. 0.01 $mm^3$, $p=0.01$). FIGS. 4A and 4B. These findings were striking due to the substantially improved efficacy over other BMP inhibitors in the literature. Pentachrome staining confirmed absence of cartilage and bone (FIG. 4A), and immunostaining further confirmed absence of Hif1α and Sox9 expression (FIG. 4B). Again, these findings were replicated using rapamycin which showed complete absence of HO in treated mice (17.5 $mm^3$ v. 0.0 $mm^3$, $p<0.001$; yes/no; $\chi2=14.3$, $p<0.001$). FIGS. 4C and 4D.

Figure 4E:
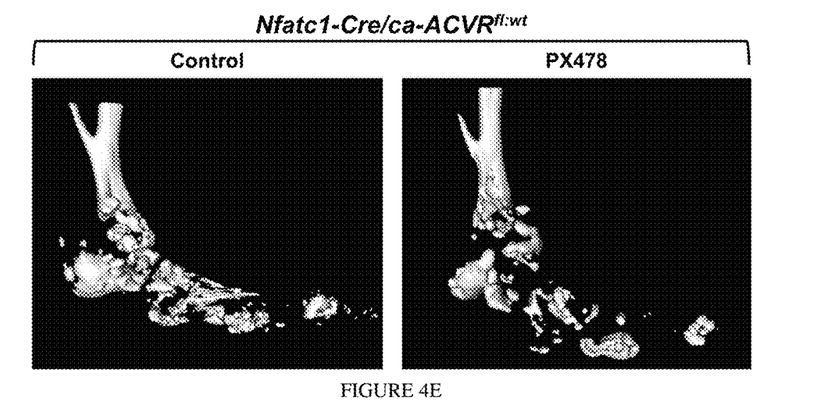
FIG. 4E illustrates ankle reconstructions of control and PX-478-treated genetic HO mice.
Figure 4F:
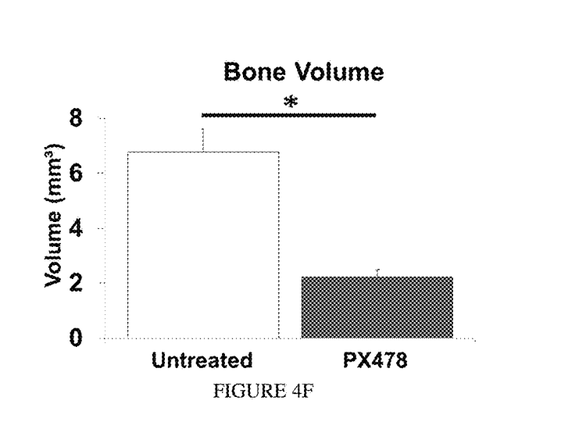
FIG. 4F is a bar graph illustrating ankle extraskeletal bone volume quantification (volume) of genetic HO mice treated with control or PX-478. (800 Hounsfield Units) (Volume: 6.8 mm³ v. 2.2 mm³, p<0.01; normalized volume: 1.0 v. 0.32, p<0.01; n=4 control treated legs; n=4 PX-478 treated legs). *p<0.05 for volumetric measurements; † p<0.05 for binary analysis (yes/no); arrow=heterotopic bone.

Lastly, PX-478 was administered to mice with congenital HO (Nfatc1-cre/caACVR1fl/fl) every other day starting from birth for two weeks. Treated mice had significantly less ectopic bone at the ankle joints when compared with mutant mice treated with vehicle (6.8 $mm^3$ v. 2.2 $mm^3$, $p<0.01$). FIGS. 4E and 4F.

Genetic loss of in mesenchymal progenitors prevents formation of heterotopic ossifications: A conditional Hif1α a knockout mouse model also was examined since global Hif1α knockout is embryonic lethal. It was first established that heterotopic ossification following burn/tenotomy consists of cells from the Prx-lineage using a series of lineage tracing experiments with Prx-cre/ROSA26mTmG mice. Importantly, it was observed that HO that formed within the soft tissue and more proximally within the soft tissue both exhibited nearly 100% presence of Prx-cre cells. In fact, it was observed that the only non-Prx-cre cells present were those forming the marrow space of the mature HO.

A mouse model of conditional Hif1α knockout in Prx-cre cells (Prx-cre/Hif1αfl/fl) was employed. These mice exhibit defective normal cartilage development. Provot, S., et al. *The Journal of cell biology* 177, 451-464 (2007). However, the impact on pathologic heterotopic ossification has not been demonstrated; therefore, burn/tenotomy was performed in Prx-cre/Hif1αfl/fl mice. Mutant mice developed minimal HO only around the calcaneus, and even these lesions were substantially smaller than in controls (5.02 $mm^3$ v. 0.18 $mm^3$, $p<0.01$). Additionally, "soft tissue" HO was nearly completely abolished in mutant mice, consistent with our findings using PX-478 treatment based on volume (0.32 $mm^3$ v. 0.01 $mm^3$) and binary analysis (yes/no; $\chi2=3.7$, $p=0.05$).

Recognizing that the conditional Hif1α knockout mouse used in this study demonstrates growth plate abnormalities, the uninjured Achilles' tendon and tibia were evaluated first. The uninjured mutant tendon cross-sectional area was 60% of the littermate control, while the uninjured mutant tibial length was 32% of the littermate control. Importantly, the histologic appearance of the tendon appeared normal, as did the tibial cortex. Due to these differences in phenotype, HO values were normalized to either cross-sectional tendon area or tibial length. As expected, the differences remained significant due to the nearly complete absence of HO in the mutant model.

On histologic evaluation with serial pentachrome stains, we were unable to identify any regions of heterotopic ossification, either near the calcaneus or within the soft tissue. Therefore, histologic evaluation showed no evidence of cartilage presence, nearly complete absence of Hif1α, and only minimal expression of Sox9 or pSmad 1/5 in mutant mice. These findings indicate that genetic loss of Hif1α in mesenchymal progenitor cells is sufficient to prevent formation of extra-skeletal bone.

Loss of Hif1α Prevents Formation of Mesenchymal Condensations in HO Models:

The HO mesenchyme of conditional Hif1α knockout mice and littermate controls was evaluated three weeks after burn/tenotomy injury. Routine histologic evaluation using H&E demonstrated absence of a mesenchymal condensation in the knockout mouse. Furthermore, immunostaining for PDGFRα, a previously described marker of mesenchymal cells within mesenchymal condensations, and SOX9 confirmed the absence of mesenchymal condensation. Similar to Hif1α knockout, PX-478 and rapamycin treatment substantially diminished the presence of mesenchymal progenitor cells and the formation of mesenchymal condensation as shown by H&E staining, as well as PDGFRα and/or SOX9 immunostaining. PDGFRα+/SOX9+ cells in sites outside of the developing HO, including the tendon-calcaneal insertion site of the uninjured hindlimb of treated or untreated mice, and Cre-conditional Hif1α knockout mice were analyzed. To confirm the effect of Hif1α inhibition on the Ad.cre/cardiotoxin model, similar staining was performed for PDGFRα/SOX9+ cells. Again, significantly diminished number of these cells in the setting of treatment two weeks after induction was observed. To demonstrate a similar decrease in these cells after early injury, Analysis of sections from the Ad.cre/cardiotoxin model 5 days after injury showed similar results, i.e. a similar decrease in PDGFRα/SOX9+ cells after injury.

Discussion

Heterotopic ossification (HO) is a pathologic process in two separate patient populations—those with severe burns and musculoskeletal trauma, and those with genetic mutations in the ACVR1 gene conferring hyperactivity. To date, emphasis has been placed on the treatment of patients with the ACVR1 mutation, and a common signaling mediator between the two forms of HO has not been identified and evaluated for therapeutic efficacy. The data described above demonstrate that Hif1α represents a common target for both forms of ectopic bone formation. Genetic loss or pharmacologic inhibition of Hif1α significantly and consistently reduced or eliminated HO. The findings are consistent in a model of trauma-induced HO with burn/tenotomy, and in two different models of genetic HO—one in which the constitutively active ACVR1 gene is activated with exogenous Ad.cre injection and cardiotoxin to stimulate inflammation (caACVR1fl/fl), and a second non-trauma model in which the constitutively active ACVR1 gene is conditionally expressed from birth (Nfatc1-cre/caACVR1fl/fl).

Transcriptome analysis showed significant up-regulation of Hif1α in adipose tissue isolated from burn patients. Mesenchymal cells with the capacity for osteogenic differentiation and which may serve as HO progenitor cells reside within adipose tissues making this an appropriate tissue type to assay. Additionally, burn patients are a critical patient population at risk for trauma-induced HO development. Patients with burn TBSA>30% have 23 times higher odds of developing HO when compared with patients with smaller surface-area burns, validating use of this cohort of patients with >20% TBSA burns for transcriptome analysis. Levi, B., et al. *The journal of trauma and acute care surgery* 79, 870-876 (2015). Ingenuity pathway analysis showed that the Hif1α signaling pathway is up-regulated in the adipose tissues of burn patients indicating downstream consequences.

In the setting of trauma-induced HO, the first step is a fibroproliferative stage that mimics the condensation event occurring during development. Both genetic loss of Hif1α in mesenchymal cells and pharmacologic inhibition of Hif1α severely impairs HO formation by preventing formation of mesenchymal condensations. In the model of conditional Hif1α knockout in Prx-cre cells, minimal HO formation was observed with almost no mesenchymal condensations or cartilage formation. Using Prx-cre/ROSA26mTmG mice, it was determined that Prx-cre positive cells form HO throughout development from early chondrogenesis to late ossification. This lineage was used to evaluate how genetic loss of Hif1α in this lineage affects HO using Prx-cre/Hif1αfl/fl mice. The absence of chondrogenesis following burn/tenotomy is consistent with studies demonstrating impaired growth plate formation in these mice. Based on the published data however, the complete absence of mesenchymal condensations at the tendon transection site was unexpected but striking. Additionally, gene knockout reduced the number of mesenchymal progenitor cells, as determined by expression of PDGFRα. Treatment or gene knockout did not alter the presence of condensing mesenchymal cells in uninjured sites (e.g. tendon-calcaneal insertion or enthesis), as these cells are not present in the absence of injury. Histologic evaluation with H&E and immunostaining for PDGFRα17-19 and SOX97 confirmed the absence of the mesenchymal condensations. Both PDGFRα and SOX9 were previously described as markers of the developing mesenchyme while H&E can also been used to identify the mesenchymal condensation. Barna, M. et al. *Nature* 436, 277-281 (2005)

In the study described herein, two different drugs, PX-478 and rapamycin, which inhibit Hif1α via different mechanisms, demonstrated a therapeutic effect on HO. PX-478 decreases Hif1α both in vitro and in vivo by decreasing Hif1α mRNA levels and blocking Hif1α mRNA translation. Constitutive VEGF signaling abrogates the effect of PX-478 on downstream angiogenic signaling confirming that its effect is up-stream of VEGF. PX-478 does not appear to alter retinoic acid signaling, a pathway previously shown to affect HO formation. Land, S. C. & Tee, A. R. *The Journal of biological chemistry* 282, 20534-20543 (2007). Rapamycin inhibits Hif1α through the mammalian target of rapamycin (mTOR). Zhang, H., et al. *Proceedings of the National Academy of Sciences of the United States of America* 105, 19579-19586 (2008). When the drugs were tested in vitro on mesenchymal cells isolated from the tendon and cultured in hypoxia, a significant decrease in Hif1α was observed. Although both PX-478 and rapamycin may have off-target effects, their shared effect on Hif1α along with results from the conditional Hif1α knockout mouse described herein indicate that pharmacologic inhibition of Hif1α prevents HO. Similar to the effect of genetic loss, pharmacologic inhibition of Hif1α significantly diminished or eliminated de novo heterotopic bone, and diminished the number of mesenchymal progenitor cells and mesenchymal condensations.

Strikingly, in the setting of ACVR1 mutation, pharmacologic Hif1α inhibition with PX-478 or rapamycin again prevented HO formation. This suggests that constitutive ACVR1 activity alone is not sufficient to induce HO, and is consistent with our clinical knowledge that patients with fibrodysplasia ossificans progressiva who have a hyperactivating mutation in ACVR1 (ACVR1 R206H) develop ectopic bone lesions following minor trauma. Similar to the burn/tenotomy model, it was observed that mesenchymal cells marked by co-expression of PDGFRα and Sox9 were present in the developing lesion of untreated mice, but eliminated in the setting of therapeutic Hif1α inhibition.

For the first time, a common target is revealed between trauma-induced and genetic HO. The findings described herein demonstrate that Hif1α inhibitors, such as PX-478 or rapamycin, are therapeutic options even for HO caused by hyperactive ACVR1 signaling.

This entire document is intended to be related as a unified disclosure, and it should be understood that all combinations of features described herein are contemplated, even if the combination of features are not found together in the same sentence, or paragraph, or section of this document. The invention also includes, for instance, all embodiments of the invention narrower in scope in any way than the variations specifically mentioned above. With respect to aspects of the invention described as a genus, all individual species are considered separate aspects of the invention. With respect to aspects of the invention described or claimed with "a" or "an," it should be understood that these terms mean "one or more" unless context unambiguously requires a more restricted meaning. If aspects of the invention are described as "comprising" a feature, embodiments also are contemplated "consisting of" or "consisting essentially of" the feature.

All publications, patents and patent applications cited in this specification are herein incorporated by reference as if each individual publication or patent application were specifically and individually indicated to be incorporated by reference.

What is claimed:

1. A method of treating a subject suffering from genetic heterotopic ossification (HO) or at risk of suffering from genetic HO, the method comprising administering to the subject rapamycin, temsirolimus, everolimus, deforolimus, zotarolimus, 32-deoxy-rapamycin, digoxin, imatinib, or PX-478.

2. The method of claim 1, comprising administering PX-478 to the subject.

3. The method of claim 1, comprising administering rapamycin to the subject.

4. The method of claim 1, wherein the subject is genetically predisposed to formation of ectopic bone lesions or has a genetic disease.

5. The method of claim 4, wherein the subject suffers from fibrodysplasia ossificans progressive (FOP).

* * * * *

UNITED STATES PATENT AND TRADEMARK OFFICE
CERTIFICATE OF CORRECTION

PATENT NO.        : 10,278,982 B2
APPLICATION NO.   : 15/373959
DATED             : May 7, 2019
INVENTOR(S)       : Benjamin Levi et al.

Page 1 of 1

It is certified that error appears in the above-identified patent and that said Letters Patent is hereby corrected as shown below:

In the Claims

At Column 16, Line 21, "progressive" should be -- progressiva --.

Signed and Sealed this
Fifteenth Day of September, 2020

Andrei Iancu
*Director of the United States Patent and Trademark Office*